United States Patent [19]
Drake

[11] 3,941,125
[45] Mar. 2, 1976

[54] TUBULAR GAUZE BANDAGE APPLICATOR

[76] Inventor: Arvel Drake, 149 Short View Drive, Des Moines, Iowa 50312

[22] Filed: Feb. 28, 1975

[21] Appl. No.: 554,130

[52] U.S. Cl. .................. 128/155; 128/157; 312/72; 221/312 A
[51] Int. Cl.² ...................................... A61F 13/00
[58] Field of Search .......................... 128/155–157, 128/165, 171; 312/45, 72; 221/312 A

[56] References Cited
UNITED STATES PATENTS

| | | | |
|---|---|---|---|
| 1,800,459 | 4/1931 | Maclean | 221/312 A |
| 2,739,587 | 3/1956 | Scholl | 128/157 |
| 2,841,809 | 7/1958 | Oliver | 221/312 A |
| 3,513,842 | 5/1970 | Keenan et al. | 128/157 |
| 3,618,750 | 11/1971 | Reiner | 312/72 |
| 3,639,130 | 2/1972 | Eichin et al. | 128/157 |

Primary Examiner—Lawrence W. Trapp
Attorney, Agent, or Firm—Henderson & Strom

[57] ABSTRACT

A cylindrical housing has a rod attached to one interior end thereof. A tube extends out of an open end of the cylindrical housing and is attached to the rod. A space is formed between the interior of the cylindrical housing and the rod such that large quantities of gauze may be received onto the rod within the housing. A flexible seal at the open end of the housing keeps the gauze within the housing clean and sterile but allows the gauze to be selectively pulled from the interior of the housing as needed. A gauze cutter is disposed around the open end of the housing. The cutter can remain stored in this position whether or not gauze is being removed. A cap is provided to cover the entire open end of the housing as well as the tube and the cutter.

19 Claims, 6 Drawing Figures

TUBULAR GAUZE BANDAGE APPLICATOR

BACKGROUND OF THE INVENTION

The present invention relates generally to a tubular bandage applicator, and more particularly to a tubular bandage applicator of an improved design which allows for sterile storage of gauze as well as for more expeditious bandage forming.

A well known method of applying tubular bandages is shown in U.S. Pat. No. 2,456,507 and 2,739,587 for example. Generally speaking, this method consists of placing some tubular gauze on a somewhat cylindrical device, placing a person's injured finger in the other end of the tubular gauze, twisting the device and thereby the gauze to draw the gauze together between the finger and the applicator and inserting the finger into the applicator such that the gauze around the applicator is folded back over the other gauze on the finger to form a completed bandage.

Heretofore this method has been employed by various types of cylindrically shaped bandage applicators such as generally shown in U.S. Pat. Nos. 2,715,903, 3,358,682, and 3,542,021. The use of such bandage applicators have been used mostly by physicians or nurses in hospitals or in the office of an attending physician. One reason for this is that these applicators must be loaded with gauze for each use, generally, and those which do provide for some storage of the gauze on the applicator for more than one bandage, do not provide a means for insuring that the gauze is kept sterile and free from dust or other air contamination. When the applicators must be loaded for each bandage, this creates a problem for the person having an injured hand who desires to administer the bandage without the help of a nurse of physician. Consequently, there is a genuine need for a commercial applicator designed for use by an injured individual, whereby a large quantity of tubular gauze may be stored in a device and in association with a bandage applicator and be kept sterile and clean while being also readily accessible.

Another problem in the prior art is that while gauze cutting structures are disclosed, for example, such in U.S. Pat. Nos. 2,715,903, 3,358,652 and 3,542,021, the cutters therefor are essentially separate from the applicator itself, and do not remain with the applicator when the gauze is being removed from the applicator. Consequently, there is always a chance that the cutter, once separated from the device, may not be immediately available when needed. There is therefore a definite need for a cutter which can remain in place on a tubular bandage applicator at all times.

SUMMARY OF THE INVENTION

The present invention relates to a tubular bandage applicator which has a storage container associated therewith for holding tubular gauze for many bandages and for keeping such gauze in a sterile environment while also allowing the gauze to be readily accessible. The present invention also relates to a tubular bandage gauze cutter which remains on the applicator at all times. A cap is provided for covering the bandage applicator cutter and generally one end of the storage structure to keep it all sterile when not in use.

An object of the present invention is to provide a tubular bandage applicator having a sterile storage structure associated therewith.

Another object of the invention is to provide a sterile gauze storage structure for a bandage applicator whereby the gauze remains in a readily accessible position.

A further object of the invention is to provide a novel cutter for a tubular bandage applicator which can remain on the applicator at all times.

Other objects, advantages, and novel features of the present invention will become apparent from the following detailed description of the invention when considered in conjunction with the accompanying drawings.

DESCRIPTION OF THE PREFERRED EMBODIMENTS

Figure 1:
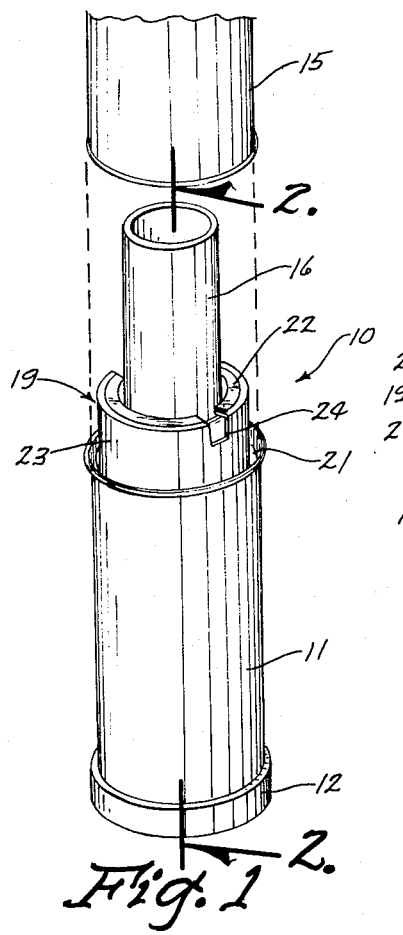
FIG. 1 is a perspective view of the present invention with the cap removed.
Figure 2:
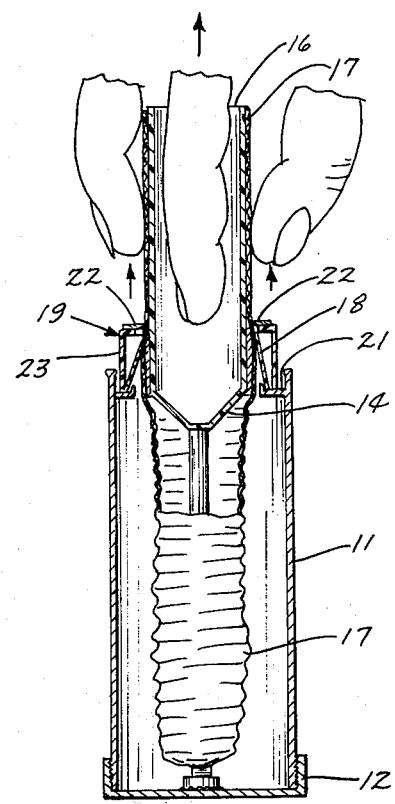
FIG. 2 is a cross-sectional view of the present invention taken along the lines 2—2 of FIG. 1 and showing the initial step for use of the applicator.

Referring now to the drawings wherein like reference numerals designate identical or corresponding parts throughout the several views, FIG. 1 shows the applicator 10 of the present invention. A cylindrical housing 11 has a bottom end 12 which is preferably threadedly attached to the remainder of the cylindrical housing 11. Threadedly engaged to this bottom end 12 is a rod 13. The upper end of the rod 13, as shown in FIG. 2, has a tapering structure 14 which provides a smooth transition surface between the rod 13 and a tube 16. A cap 15 is provided for the top of the housing 11.

Preferably, the tube 16 and the rod structure 13 would be manufactured in a unitary fashion and the gauze 17 (FIG. 2) would be placed thereon as shown in FIG. 2. Once this is accomplished the entire unit including the rod 13, the tube 16 and the gauze 17 would be threadedly screwed into the bottom end 12 of the housing 11. A seal 18, preferably of a soft plastic material, would be connected to the top of the housing 11 in order to keep the interior of the housing 11 sterile and thereby the stored gauze 17 from becoming contaminated by dust or other air contamination. The seal 18 is flexible enough to exert continual pressure at the top end thereof against the gauze 17 as it passes over the tube 16, but this resistance is small enough to allow the gauze 17 to be easily removed from the interior of the housing 11 and along the tube 16.

Figure 5:
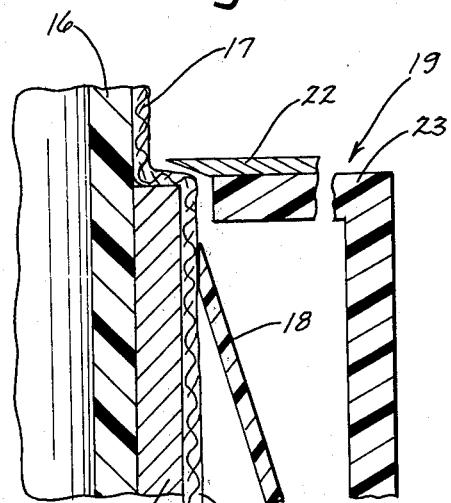
FIG. 5 is an enlarged cross-sectional view showing a cutting device and a seal in association with the applicator of the present invention.

A cutting mechanism 19 is then inserted over the tube 16 such that it rests upon a surface 21 on the top of the housing 11. The cutter 19 has a pair of arcuately shaped blades 22 which are bonded to or otherwise supported on an annular flexible member 23. This annular flexible member 23 has a pair of slots 24 disposed directly across from one another in the flexible member 23. A ring member 26 (FIG. 5) also operates in conjunction with the cutter 19 to allow for quick and efficient cutting of the gauze as desired. It is noted that the cutter 19 can be easily operated with one hand to thereby allow a person to change a finger bandage without help from others.

Figure 6:
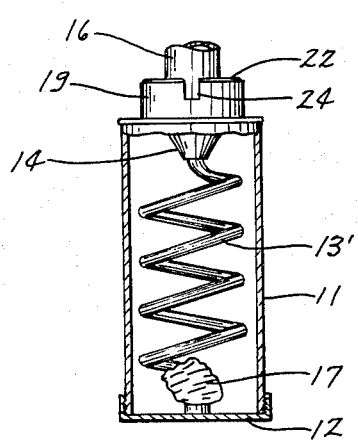
FIG. 6 shows a partial cross-sectional view of a modified form of the present invention.

The FIG. 6 embodiment of the present invention is identical to the embodiment of FIGS. 1 - 5 except for the fact that the rod 13' is of a coil, spiral or helical configuration. The purpose of this configuration of rod 13' is to allow a larger quantity of gauze 17 to be stored within the housing 11 of the tubular bandage application 10'.

Figure 3:
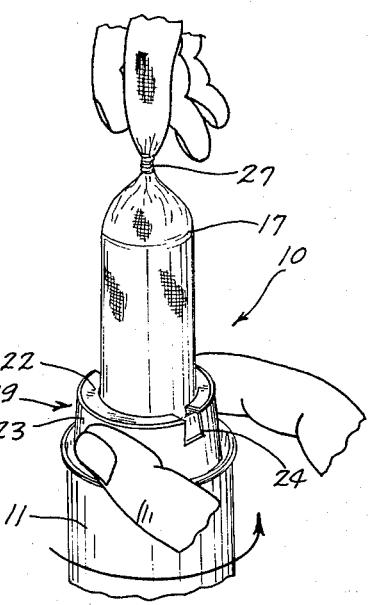
FIG. 3 is a partial perspective view of the present invention showing the cutting step for using the present invention.
Figure 4:
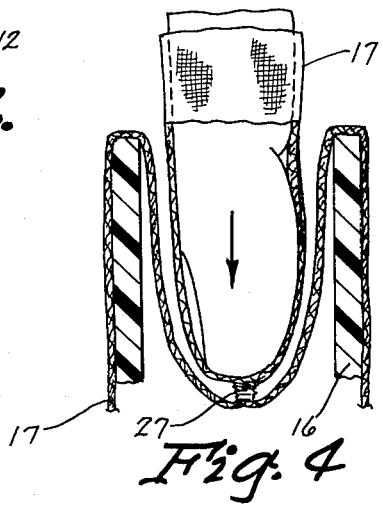
FIG. 4 is a partial cross-sectional view of the present invention showing the final step for use of the disclosed applicator.

In operation, a person wishing to bandage a finger would insert that finger into tube 16 as shown in FIG. 2. The gauze 17 which is directly disposed around the tube 16 would then be grasped and pulled upwardly by the other fingers on the same hand as the injured finger. Once the end of the injured finger having the gauze therearound is an inch or two from the end of the tube 16, the entire applicator 10 is rotated to form a twisted juncture 27 as clearly shown in FIG. 3. The above mentioned steps may be repeated several times in order to form a thicker bandage, but the last layer of the bandage would be formed by utilizing the cutter 19 as shown in FIG. 3 In FIG. 3 the cutter 19 is squeezed such that the flexible or resilient annular member 23 flexes so that the cutters 22 move inwardly and contact the gauze around the tube 16. This movement of the cutters 22 is allowed because of the slots 24 formed in the flexible annular member 23. A rotating movement is then applied to the cutter 19 with respect to the tube 16. Once the gauze 17 is cut by the cutter 19 the last step is performed as shown in FIG. 4 by merely pushing the finger to be bandaged inwardly such that the portion of the tubular gauze remaining on the tube 16 is folded back over the injured finger to form a completed bandage.

Accordingly, it can be seen that the disclosed embodiment of the present invention does indeed accomplish the objects set forth above to provide a very useful and commercially desirable product. Obviously many modifications and variations of the present invention are possible in light of the above teachings. It is therefore to be understood that, within the scope of the appended claims, the invention may be practiced otherwise than as specifically described.

I claim:

1. A tubular bandage applicator comprising:
   a substantially hollow housing having an opening therein;
   a rod connected at one end thereof to the interior of said hollow housing;
   a tube connected to the other end of said rod;
   said rod and said tube being adapted to coaxially receive tubular gauze thereon.

2. An applicator as defined in claim 1 wherein said tube extends out of the opening in said hollow housing.

3. An applicator as defined in claim 2 including cap means for covering said tube and said opening in the housing.

4. An applicator as defined in claim 2 having sealing means for sealing the interior of the housing from the surrounding air.

5. An applicator as defined in claim 4 wherein said sealing means is connected to said housing and surrounds said tube.

6. An applicator as defined in claim 1 wherein said rod is substantially smaller in diameter than said tube to permit more gauze to be stored thereon.

7. An applicator as defined in claim 6 wherein said rod is substantially straight.

8. An applicator as defined in claim 6 wherein said rod is substantially helical to permit more gauze to be stored thereon.

9. An applicator as defined in claim 6 wherein the connection of the tube to the rod comprises tapering means to provide a smooth transition between the rod and the tube so that the gauze will freely pass from the rod to the tube.

10. An applicator as defined in claim 9 wherein said tube has one open end, said tube further having a gauze cutting surface thereon spaced from said one open end of the tube by a distance of approximately an average human finger length.

11. An applicator as defined in claim 1 including means for cutting gauze.

12. An applicator as defined in claim 11 wherein said gauze cutting means comprises an arcuately shaped cutting blade.

13. An applicator as defined in claim 12 wherein said gauze cutting means further comprises an annular flexible member adapted to be received around said tube, slot means being formed in one end of said annular flexible member for allowing flexing of said one end of said cutter, said arcuately shaped blade being received on said one end and adapted to cut gauze received on said tube when said annular member is flexed inwardly and rotated.

14. An applicator as defined in claim 13 wherein said cutting means further comprises a second arcuately shaped cutter disposed on said one end of said annular flexible member opposite the first said cutting blade.

15. An applicator as defined in claim 14 wherein said cutting blades lie in a plane normal to the axis of said tube.

16. An applicator as defined in claim 13 including an annular surface on said housing for supporting and storing said cutting means.

17. An applicator as defined in claim 16 including cap means for covering said tube, said cutting means and the opening in the housing.

18. An applicator as defined in claim 1 wherein said rod is removably attached to said housing.

19. An applicator as defined in claim 18 wherein said housing is cylindrical in shape and said rod is connected to an interior end of said housing.

* * * * *